United States Patent [19]
Nakagiri et al.

[11] Patent Number: 5,720,864
[45] Date of Patent: Feb. 24, 1998

[54] ELECTROCHEMICAL DEVICE

[75] Inventors: Yasushi Nakagiri, Tsuzuki-gun; Noboru Taniguchi, Osaka; Takaharu Gamou, Fujiidera, all of Japan

[73] Assignee: Matsushita Electric Industrial Co., Ltd., Osaka-fu, Japan

[21] Appl. No.: 717,451

[22] Filed: Sep. 20, 1996

[30] Foreign Application Priority Data

Sep. 28, 1995 [JP] Japan .................. 7-251232
Feb. 22, 1996 [JP] Japan .................. 8-035235

[51] Int. Cl.$^6$ ............................ G01N 27/26
[52] U.S. Cl. .......... 204/421; 204/424; 204/425; 429/30; 429/33; 429/191; 429/193
[58] Field of Search ................ 429/30, 33, 193, 429/191; 204/421, 425, 424

[56] References Cited

U.S. PATENT DOCUMENTS

| | | | |
|---|---|---|---|
| 4,851,303 | 7/1989 | Madou et al. | 429/13 |
| 4,948,680 | 8/1990 | Madou et al. | 429/13 |
| 5,001,021 | 3/1991 | Marticle et al. | 429/193 |
| 5,134,042 | 7/1992 | Madou et al. | 429/13 |
| 5,387,330 | 2/1995 | Taniguchi et al. | 429/33 |
| 5,403,461 | 4/1995 | Tuller et al. | 204/252 |
| 5,629,103 | 5/1997 | Wersing et al. | 429/30 |

FOREIGN PATENT DOCUMENTS

| | | |
|---|---|---|
| 64-87510 | 3/1989 | Japan . |
| 7-65839 | 3/1995 | Japan . |
| 7-167833 | 7/1995 | Japan . |

*Primary Examiner*—Bruce F. Bell
*Attorney, Agent, or Firm*—Panitch Schwarze Jacobs & Nadel, P.C.

[57] ABSTRACT

There is disclosed an electrochemical device such as a fuel cell, oxygen sensor, oxygen pump or the like, in which a barium-cerium complex oxide is used as an electrolyte. This device comprises a cathode formed on one surface of a layer of the barium-cerium complex oxide and an anode formed on another surface of the layer, and at least one of the anode and the cathode is formed to have a layered structure comprising a first thin film electrode formed on the layer of the barium-cerium complex oxide and a second electrode formed on the first thin film electrode. Further, at least one electrode comprises a mixture of platinum and one element selected from the group consisting of gold, silver, copper and carbon.

10 Claims, 7 Drawing Sheets

5,720,864

ELECTROCHEMICAL DEVICE

BACKGROUND OF THE INVENTION

1. Field of the Invention

The present invention relates to an improvement of an electrochemical device using an oxygen ion conductive solid electrolyte, especially of an electrode for a limiting current type oxygen sensor using a barium-cerium complex oxide as a solid electrolyte.

2. Description of the Prior Art

As an electrochemical device, there are various known devices utilizing an ion conductive solid electrolyte. Especially, examples of representative devices utilizing an oxygen ion conductive solid electrolyte include a fuel cell, oxygen pump, oxygen sensor and the like. Among them, the oxygen sensor, particularly a limiting current type oxygen sensor will be described herein.

Conventionally, a stabilized zirconia solid electrolyte is usually used for the limiting current type oxygen sensor. A conventional limiting current type oxygen sensor is shown in FIG. 6. As shown in the figure, a cathode 7 and an anode 8 are formed on both sides of an oxygen ion conductive solid electrolyte 1; on the cathode 7 side, there is mounted an oxygen diffusion-resistant member 5 made of ceramics, for example, having a diffusion pore 6 for restricting oxygen diffusion.

In the above-described configuration, when a voltage is applied between the cathode 7 and the anode 8, there occur a series of motions such that oxygen receives electrons and changes to oxygen ions at the cathode 7, the oxygen ions then migrate in the solid electrolyte 1 and discharge electrons at the anode 8 to produce a molecule of oxygen, as a result of which a current flows in a closed circuit. In the absence of a diffusion pore for limiting oxygen diffusion, oxygen is likely to be supplied to the cathode 7 in response to an applied voltage, which results in increased output current. In this limiting current type oxygen sensor, however, since the diffusion pore provided on the cathode 7 effectively restricts the oxygen diffusion, the amount of supplied oxygen reaches a saturated value even if the applied voltage exceeds a certain constant value. As a result, the oxygen sensor shows a constant limiting current value as shown in FIG. 7. The value is substantially proportional to the oxygen concentration in a tested gas. This means that upon application to the limiting current type oxygen sensor of a certain high voltage generating a limiting current, there occurs a current flow proportional to the oxygen concentration of a specimen. Therefore, the oxygen concentration can be grasped easily only by reading the current value on the oxygen sensor.

In such mode, the limiting current type oxygen sensor can conveniently detect oxygen from low oxygen concentrations to high oxygen concentrations. However, when stabilized zirconia is used as the oxygen ion conductive solid electrolyte, the oxygen sensor should be operated at an elevated temperature from about 500° C. to 800° C. because of high inner electrical resistance of the solid electrolyte. Therefore, the oxygen sensor of this type has several drawbacks including accelerated deteriorations of heater, adiabatic construction and sensor performance, and an oxygen ion conductive solid electrolyte which operates at lower temperatures has been desired.

In this circumstance, a limiting current type oxygen sensor using a barium-cerium complex oxide is noted. Since this material has a higher ionic conductivity and lower activation energy for ion migration than stabilized zirconia, the limiting current value is manifested even at a lower temperature of 300° C. to 350° C., and oxygen concentration can be detected.

However, with respect to the barium-cerium complex oxide which can operate at lower temperatures, following problems occur when the same platinum electrode is applied as in the stabilized zirconia. Namely, the platinum electrode allows satisfactory detection of oxygen at early stage. But, when successive operations are conducted in an atmosphere at 300° C. in air while a voltage of 1.0 V being applied between a platinum anode and a platinum cathode, the current value finally decreases as shown in FIG. 8 and the limiting current is not attained, resulting in a short service life. One of the reasons for this may be that electrical resistance on an electrode-electrolyte interface increases with the progress of chemical reaction between the electrode and the solid electrolyte.

Usually, an electrode is formed by printing. This method, however, produces reaction products as a result of reaction of a substance such as an organic binder or a glass frit included in a metal containing ink paste for enhancing firing and adhesion of the paste with the barium-cerium complex oxide, and these products enhance electrical resistance on the electrode-electrolyte interface.

Another reason is that when an electrode which can be used for zirconia is applied to a barium-cerium complex oxide without any treatment, stress is formed in the surface portion and physical separation of the electrode may occur due to a difference in thermal expansion coefficient between the barium-cerium complex oxide and the stabilized zirconia.

To cope with the difference in thermal expansion coefficient, it is believed a good idea that a metal having a large thermal expansion coefficient such as gold, silver or copper is used to produce an electrode. Changes in output current value were examined when gold was used as an electrode and a voltage was applied successively at varied temperatures. Consequently, as shown in FIG. 8, output current value is high and very stable even with a lapse of time at 400° C.; however, at 300° C. and 350° C., activation degree of the electrode is low in comparison with the platinum electrode, and deterioration has progressed though gold is more stable than platinum. To overcome such circumstances and to carry out a stable operation even at a low temperature of around 300° C., it is necessary to raise the activity of an electrode which is stable but has a low activity.

Countermeasures against deteriorated electrode-electrolyte interfaces to overcome these phenomena remain a serious issue for assessing the oxygen detection life of the limiting current type oxygen sensor using the barium-cerium complex oxide.

Further, the issue regarding deteriorated electrode-electrolyte interfaces may also apply to other electrochemical devices such as an oxygen pump and a fuel cell using the barium-cerium complex oxide as an electrolyte.

SUMMARY OF THE INVENTION

An object of the present invention is to provide an electrochemical device which solves the above-described problem regarding the electrode-electrolyte interfaces and allows a long-term stable operation.

Another object of the present invention is to provide a limiting current type oxygen sensor which allows a stable long-term operation.

The present invention solves the foregoing problems by configuring at least either one of anode and cathode so as to alleviate the difference in thermal expansion coefficient from a barium-cerium complex oxide solid electrolyte.

In one aspect of the present invention, a thin film electrode composed of pure material completely free from organic binder and glass frit is inserted between a cathode and/or an anode and a barium-cerium complex oxide solid electrolyte.

The present invention provides an electrochemical device comprising a layer of a barium-cerium complex oxide, a cathode formed on one surface of the layer of the barium-cerium complex oxide and an anode formed on another surface of the layer of the barium-cerium complex oxide, at least either one of the anode and cathode being formed to have a two-layered structure comprising a layer of a first thin film formed on a surface of the layer of the barium-cerium complex oxide and a layer of a second electrode formed thereon.

In another aspect of the present invention, the above-mentioned problems are solved by using a mixture obtained by mixing a small amount of platinum with one substance selected from the group consisting of gold, silver, copper and carbon, for an electrode for an electrochemical device using the barium-cerium complex oxide.

In a preferred mode of the present invention, the barium-cerium complex oxide is an oxide represented by the formula:

wherein M is at least one element selected from the group consisting of Sc, Y, La, Pt, Nd, Pm, Sm, Eu, Gd, Tb, Dy, Ho and Er, "x" is defined by $0<x<1$, and oxygen deficiency "a" is defined by $0<a<1$.

Further, it is preferred that $0.16 \leq x \leq 0.28$.

In another mode of the present invention, the barium-cerium complex oxide is an oxide represented by the formula $BaCe_{1-x}Gd_xO_{3-a}$, wherein $0.16 \leq x \leq 0.28$ and $0<a<1$.

Further, the first thin film electrode of the anode or the cathode is preferably composed of Pt, Pd, Au or Ag.

In another preferred mode of the present invention, a mixing ratio of platinum in the electrode is not more than 5% by atom.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE PREFERRED EMBODIMENTS

In the present invention, at least one of the anode and the cathode being formed to have the two-layered structure comprising the first thin film electrode formed on the layer of the barium-cerium complex oxide and the second electrode formed thereon. This structure effectively prevents formation of resistance raising substances on the electrode-electrolyte interfaces by isolating the solid electrolyte from an organic binder or glass frit included in an ink paste for printing. Further, since the layer of the first thin film electrode readily adheres to the barium-cerium complex oxide, the difference in thermal expansion coefficient between the electrode material and the electrolyte can be well alleviated. The subsequent lamination of the second electrode realizes two-staged alleviation of the difference in thermal expansion coefficient.

Also, the present invention uses for an electrode a mixture obtained by mixing a small amount of platinum with one substance selected from the group consisting of gold, silver, copper and carbon. As a result, the thermal expansion coefficient, of the electrode becomes physically much compatible with that of the barium-cerium complex oxide, and the electrode itself is active and generates stable outputs even at low temperatures because of catalytic effect.

Namely, a limiting current type oxygen sensor can be obtained in which deterioration of electrode is small and the life is long. With the use of the solid electrolyte having a high ionic conductivity, it is possible to produce a small size oxygen sensor which operates at low temperatures and has a high sensitivity compared to the conventional oxygen sensor using stabilized zirconia.

Therefore, there can be produced a simple and compact oxygen sensor with high accuracy and reliability at low cost, in comparison with the conventional limiting current type oxygen sensor using stabilized zirconia.

In the following paragraphs, preferred embodiments of the present invention will be described by way of examples with reference to the attached drawings.

EXAMPLE 1

Figure 1:
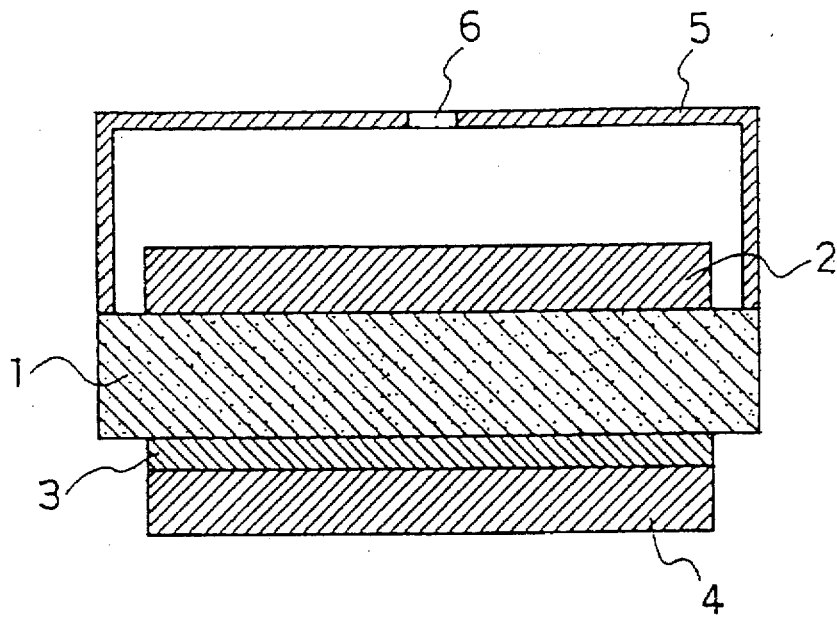
FIG. 1 is a cross-sectional view showing one example of the oxygen sensor in accordance with the present invention.

FIG. 1 is a longitudinal sectional view of one example of the oxygen sensor in accordance with the present invention.

A cathode 2 is formed on one surface of a solid electrolyte layer 1. On another surface of the electrolyte layer 1, an anode having two layers consisting of a first thin film electrode 3 and a second electrode 4 is formed. Further, on the cathode 2 side, an oxygen diffusion resistant member 5 having a diffusion pore 6 for regulating oxygen molecule diffusion is provided.

As the solid electrolyte, barium-cerium-gadolinium oxide $BaCe_{0.8}Gd_{0.2}O_{3-a}$ was used. This oxide is perovskite type oxide, and is thermally stable. Usually, most of oxides of this type are unstable in a reducing atmosphere, but this oxide is stable even in a reducing atmosphere. This solid electrolyte was made into a sheet of 10 mm×10 mm having a thickness of 0.45 mm.

Platinum was used for the cathode 2. Namely, a thick film (4 to 5 μm) of platinum paste was formed by screen printing method, and the thick film was fired at 900° C. for one hour to form the cathode. The first thin film electrode 3 of the anode was formed using a sputtered platinum film (<1 μm).

And, the second electrode 4 of the anode was formed by laminating a platinum paste on the surface of the sputtered platinum film by screen printing and firing, in the same manner as applied for the cathode 2. Further, an oxygen diffusion resistant member 5 was fixed to the solid electrolyte layer 1 on the cathode 2 side, using a glass paste.

Figure 4:
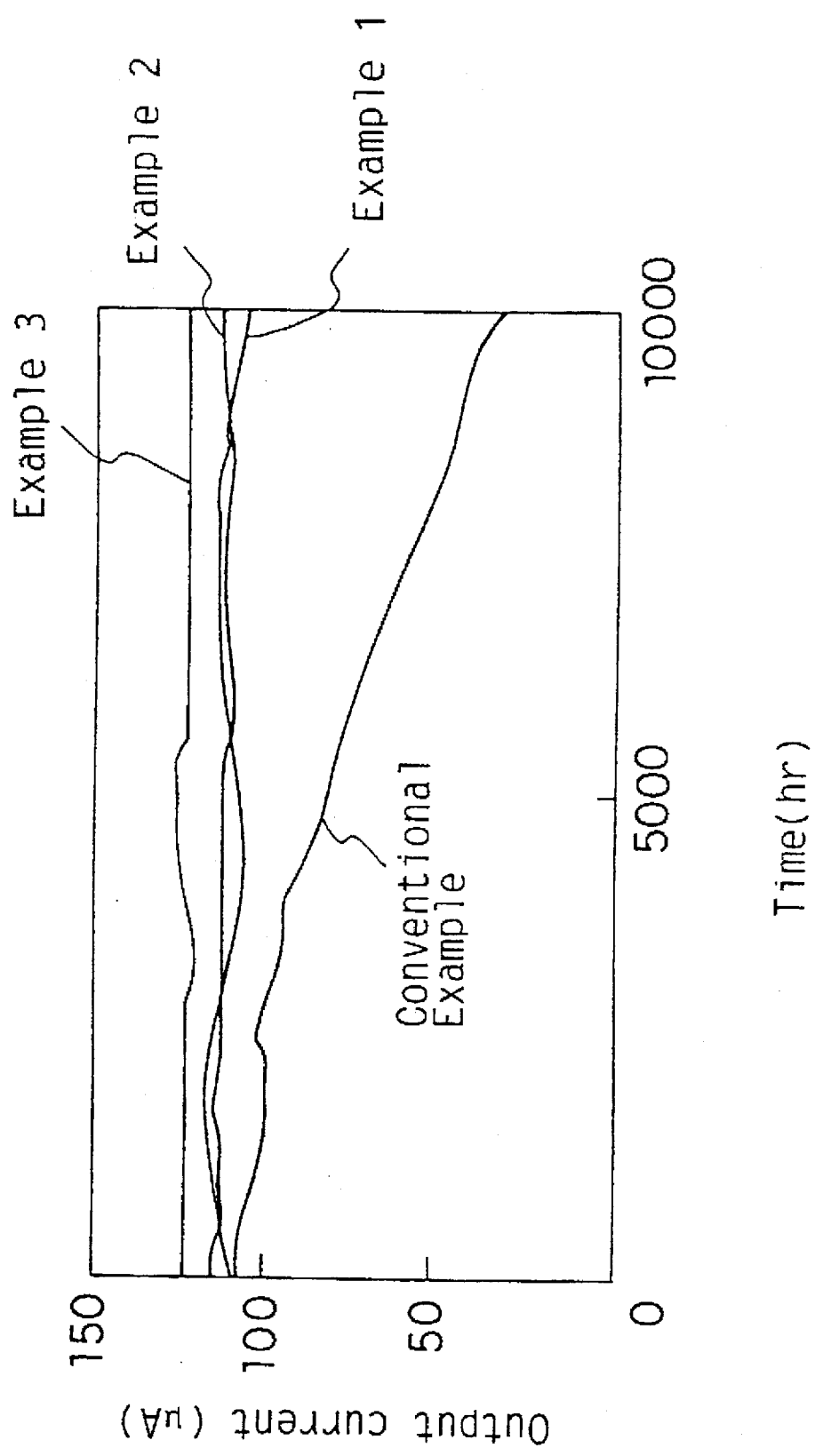
FIG. 4 is a graph showing changes in output current value of the oxygen sensor with a lapse of time.

When voltage-ampere characteristics were measured in this oxygen sensor, it was observed that the current value was a little higher than that observed in an oxygen sensor lacking the thin film electrode 3. Even at 300° C., a satisfactory limiting current characteristic was observed in this oxygen sensor. When a voltage of 1.0 V was applied to this sensor, the limiting current observed was proportional to the oxygen concentration. This oxygen sensor was subjected to a consecutive test by applying a voltage of 1.0 V at 300° C. to examine sequential changes in the output current. As a result, this oxygen sensor maintained extremely excellent stability for a long time, compared to the conventional example as shown in FIG. 4.

That is, by adopting a constitution in which the thin film electrode 3 is inserted between the solid electrolyte 1 and the electrode 4 of the anode, it is possible to produce a limiting current type oxygen sensor having a long service life with less adverse change in output current, allowing a stable operation at low temperatures, compared to the conventional oxygen sensor.

EXAMPLE 2

Figure 2:
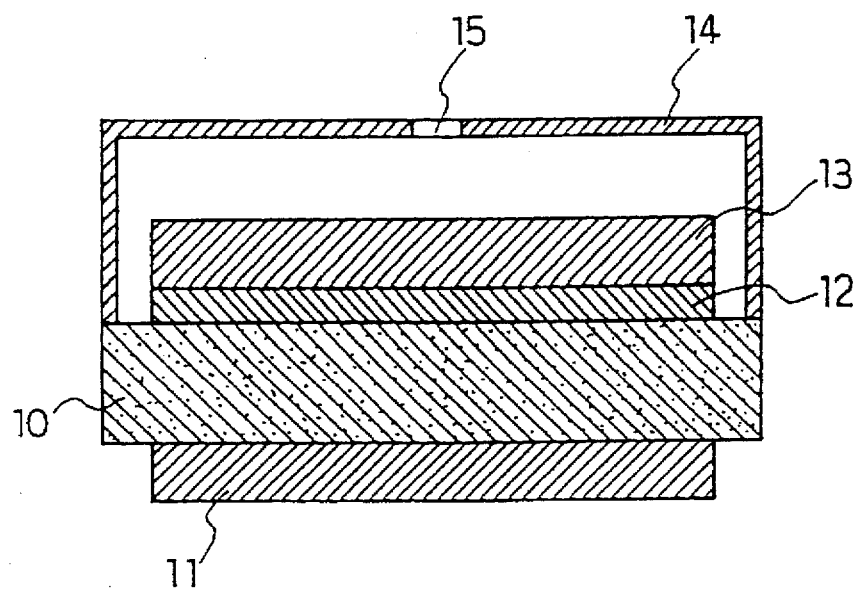
FIG. 2 is a cross-sectional view showing another example of the oxygen sensor in accordance with the present invention.

FIG. 2 is a longitudinal sectional view of another example of the oxygen sensor in accordance with the present invention.

A anode 11 is formed on one surface of a solid electrolyte layer 10. On another surface of the electrolyte layer 10, a cathode having two layers consisting of a first thin film electrode 12 and a second electrode 13 is formed. Further, on the electrode 13 side, there is provided an oxygen diffusion resistant member 14 having a diffusion pore 15 for regulating oxygen molecule diffusion.

In the present example, as the solid electrolyte, barium-cerium-yttrium oxide $BaCe_{0.8}Y_{0.2}O_{3-a}$ was used. The process for producing this oxygen sensor was substantially the same as that applied in Example 1, except that the film electrode 12 was formed on the cathode 13 side.

Also in this example, the oxygen sensor showed the limiting current characteristic at 300° C. and the limiting current was proportional to the oxygen concentration. When the oxygen sensor was subjected to the same life test as applied for Example 1, it showed substantially the same current value as in Example 1, with a relatively stable, continuous, and long-term output characteristic, compared with the conventional example, as shown in FIG. 4.

In this way, in the presence of the thin film electrode 12 also in the cathode, it is possible to produce a limiting current type oxygen sensor having a long service life with less adverse change in output current, allowing stable operation at low temperatures, compared to the conventional oxygen sensor.

EXAMPLE 3

Figure 3:
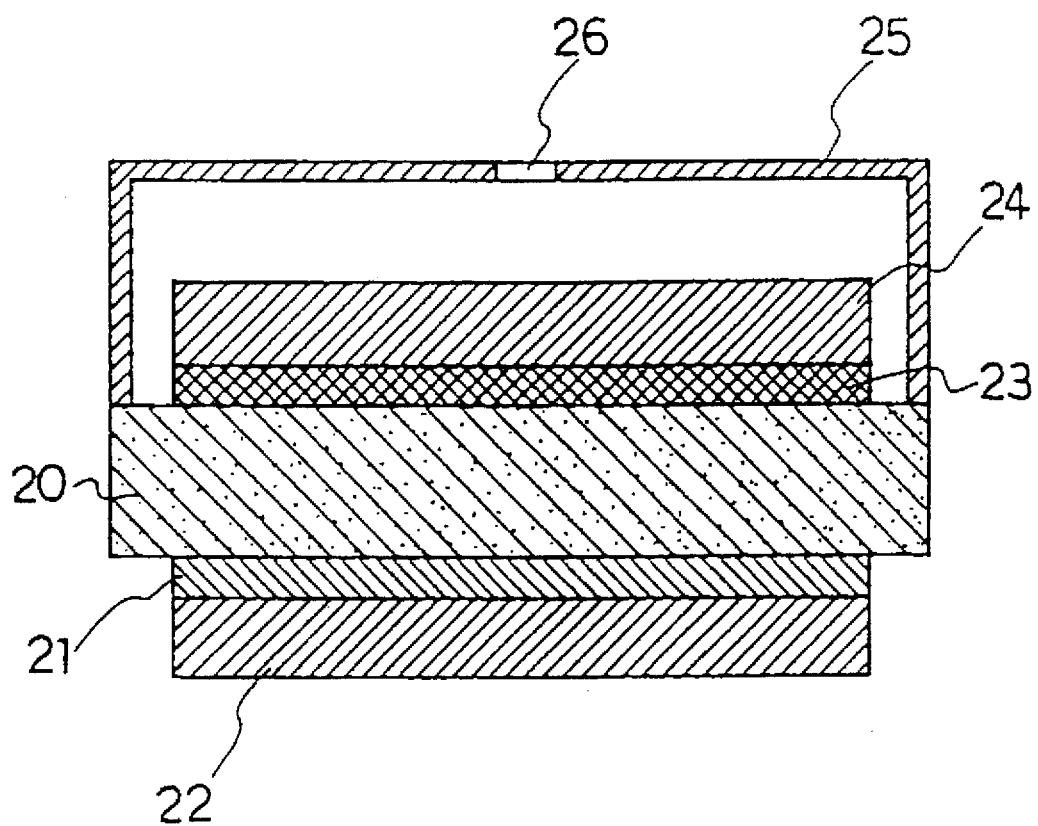
FIG. 3 is a cross-sectional view showing still another example of the oxygen sensor in accordance with the present invention.

FIG. 3 is a longitudinal sectional view of another example of the oxygen sensor in accordance with the present invention.

An anode having two layers consisting of a first thin film electrode 21 and a second electrode 22 are formed on one surface of a solid electrolyte layer 20. On another surface of the electrolyte layer 20, a cathode having two layers consisting of a first thin film electrode 23 and a second electrode 24 is formed. Further, on the cathode electrode 24 side, there is provided an oxygen diffusion resistant member 25 having a diffusion pore 26 for regulating oxygen molecule diffusion.

In the present example, as the solid electrolyte, barium-cerium-gadolinium oxide $BaCe_{0.84}Gd_{0.16}O_{3-a}$ having a different gadolinium content from that of Example 1 was used. The process for producing this oxygen sensor was substantially the same as that applied in Examples 1 and 2, except that the thin film electrode 21 was formed on the anode side and the thin film electrode 23 was formed on the cathode side, respectively.

Also in this example, the oxygen sensor showed the limiting current characteristic at 300° C. and the limiting current was proportional to the oxygen concentration. When the oxygen sensor was subjected to the same life test as applied for Examples 1 and 2, it showed a little higher value than those observed in Examples 1 and 2, with a relatively stable, continuous, and long-term output characteristic, compared with the conventional example, as shown in FIG. 4.

In this way, in the presence of the thin film electrode 21 on the anode side and the thin film electrode 23 on the cathode side, it is possible to produce a limiting current type oxygen sensor having a long service life with less adverse change in output current, allowing stable operation at low temperatures, compared to the conventional oxygen sensor.

In addition to the effects observed in Examples 1 and 2, this example showed an additional effect of increased output current. Further, this example has still another effect of elongated service life because the structure of this example simultaneously solves the issue of deteriorations in the anode and cathode.

EXAMPLE 4

As a solid electrolyte, the same barium-cerium-gadolinium oxide $BaCe_{0.8}Gd_{0.23-a}$ as applied in Example 1 was used. This solid electrolyte was made into a sheet of 10 mm×10 mm having a thickness of 0.45 mm. A mixture obtained by mixing 1 to 11% by atom of platinum with gold was used for a cathode and an anode, respectively. Namely, a thick film (4 to 5 μm) was formed by screen printing method, and the thick film was fired at 900° C. for one hour to form an electrode. Further, an oxygen diffusion restricting plate was fixed to the solid electrolyte layer on the cathode electrode side by using a glass paste.

Figure 5:
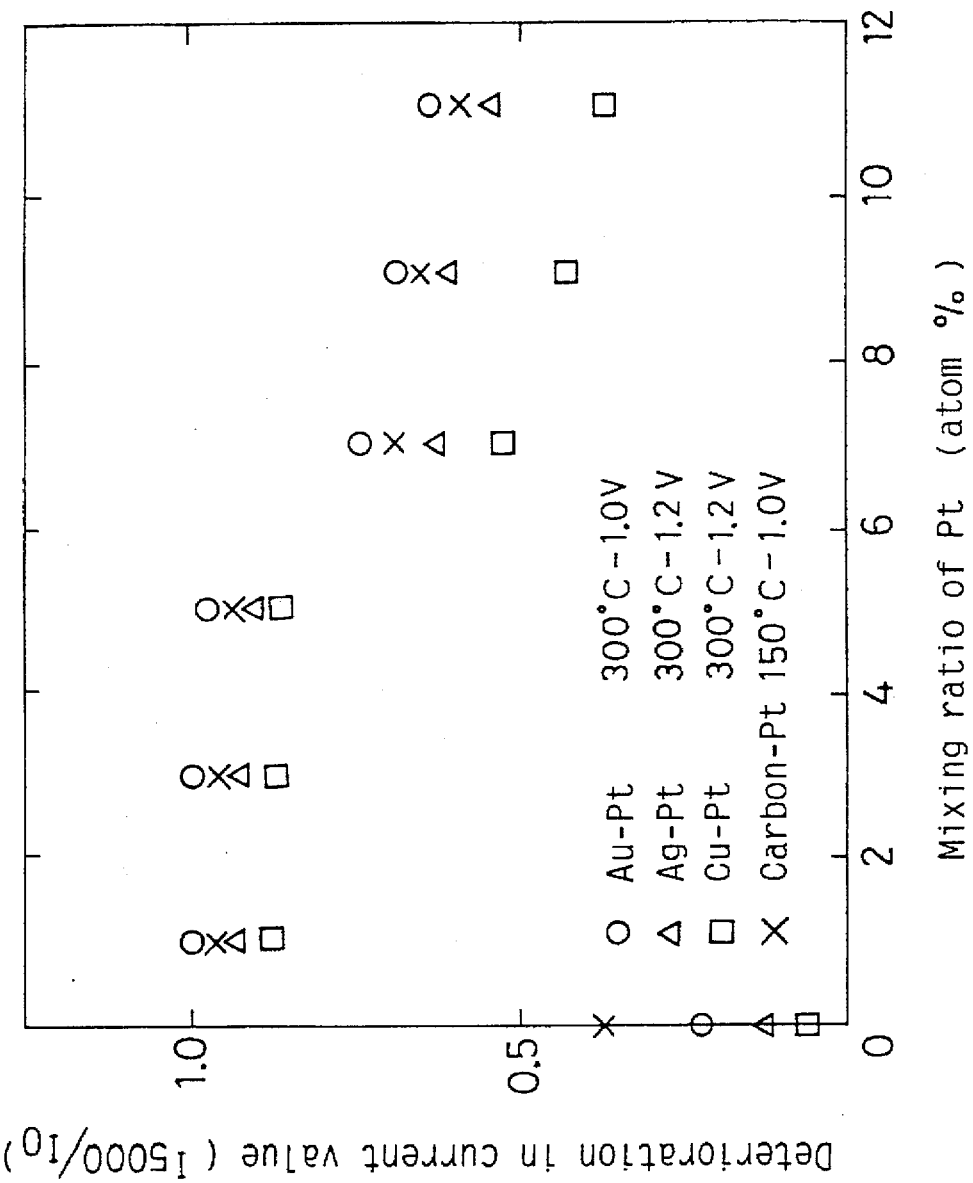
FIG. 5 is a graph showing the results of life tests of the electrochemical devices using various electrodes.
Figure 6:
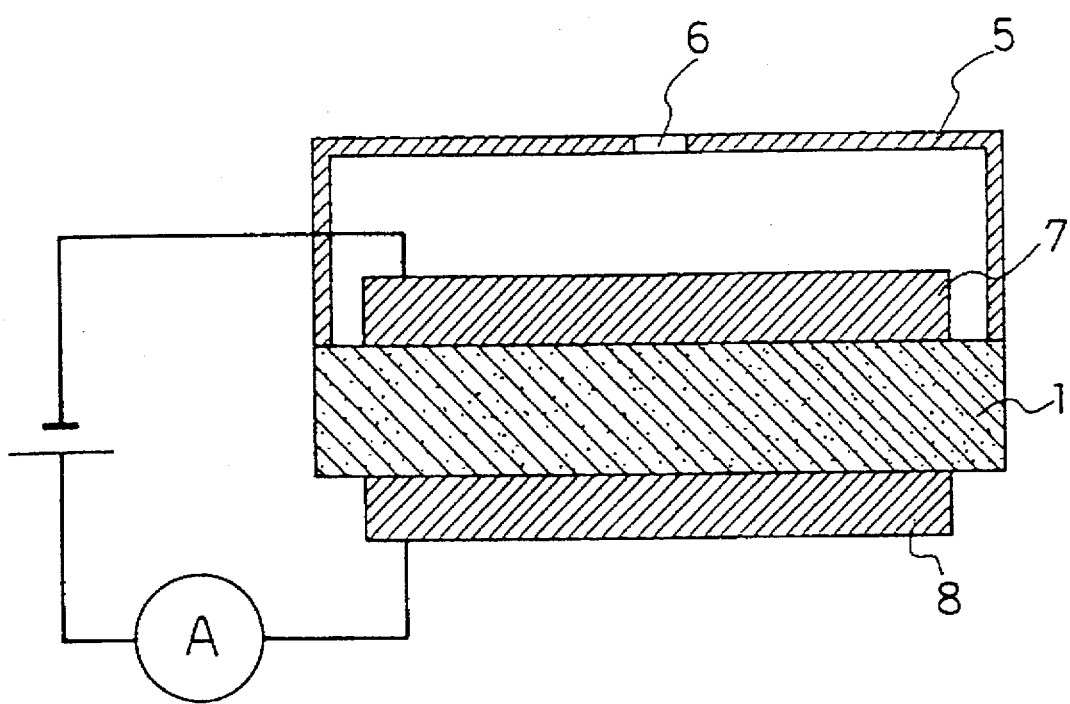
FIG. 6 is a cross-sectional view showing a conventional limiting current type oxygen sensor.
Figure 7:
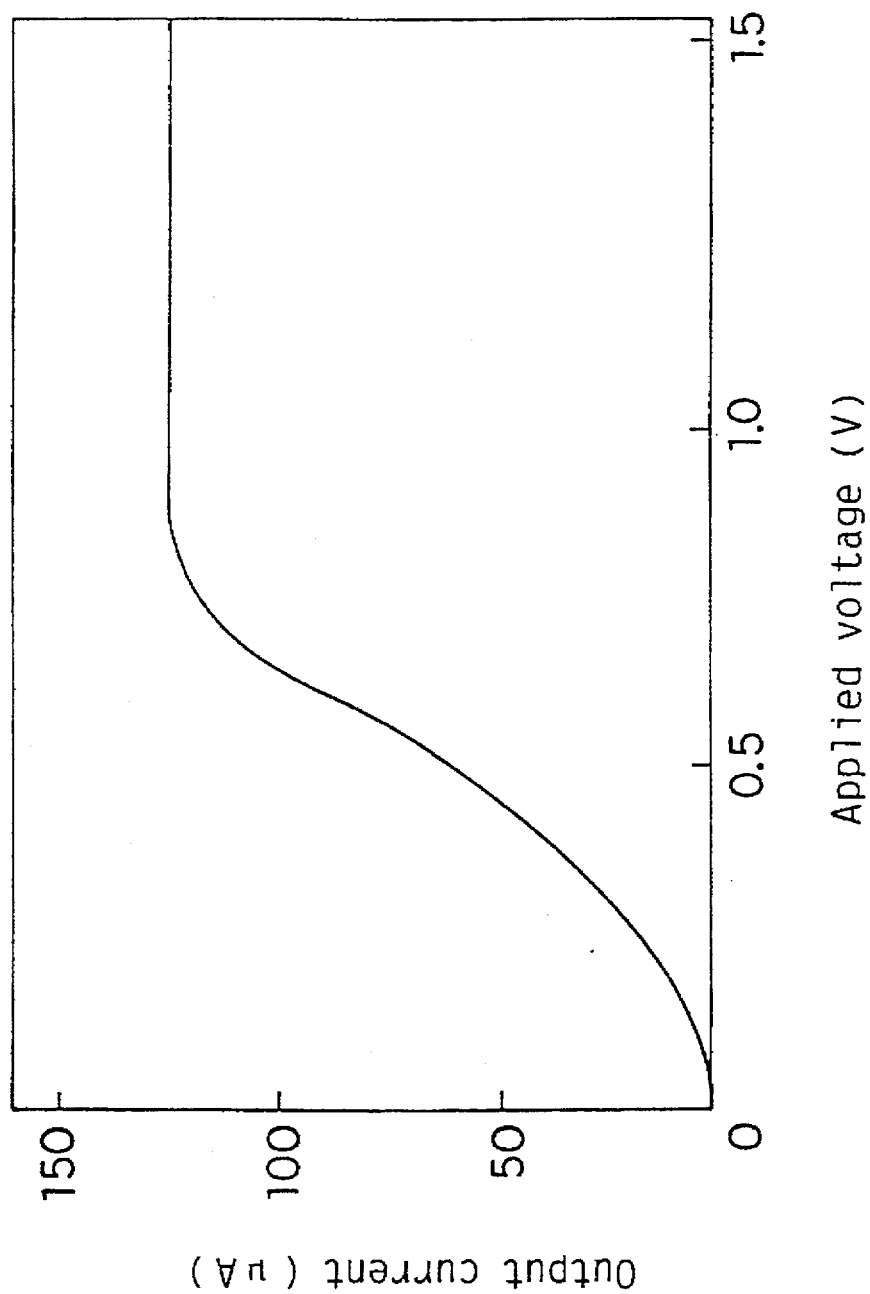
FIG. 7 is a graph showing limiting current features in the conventional limiting current type oxygen sensor.
Figure 8:
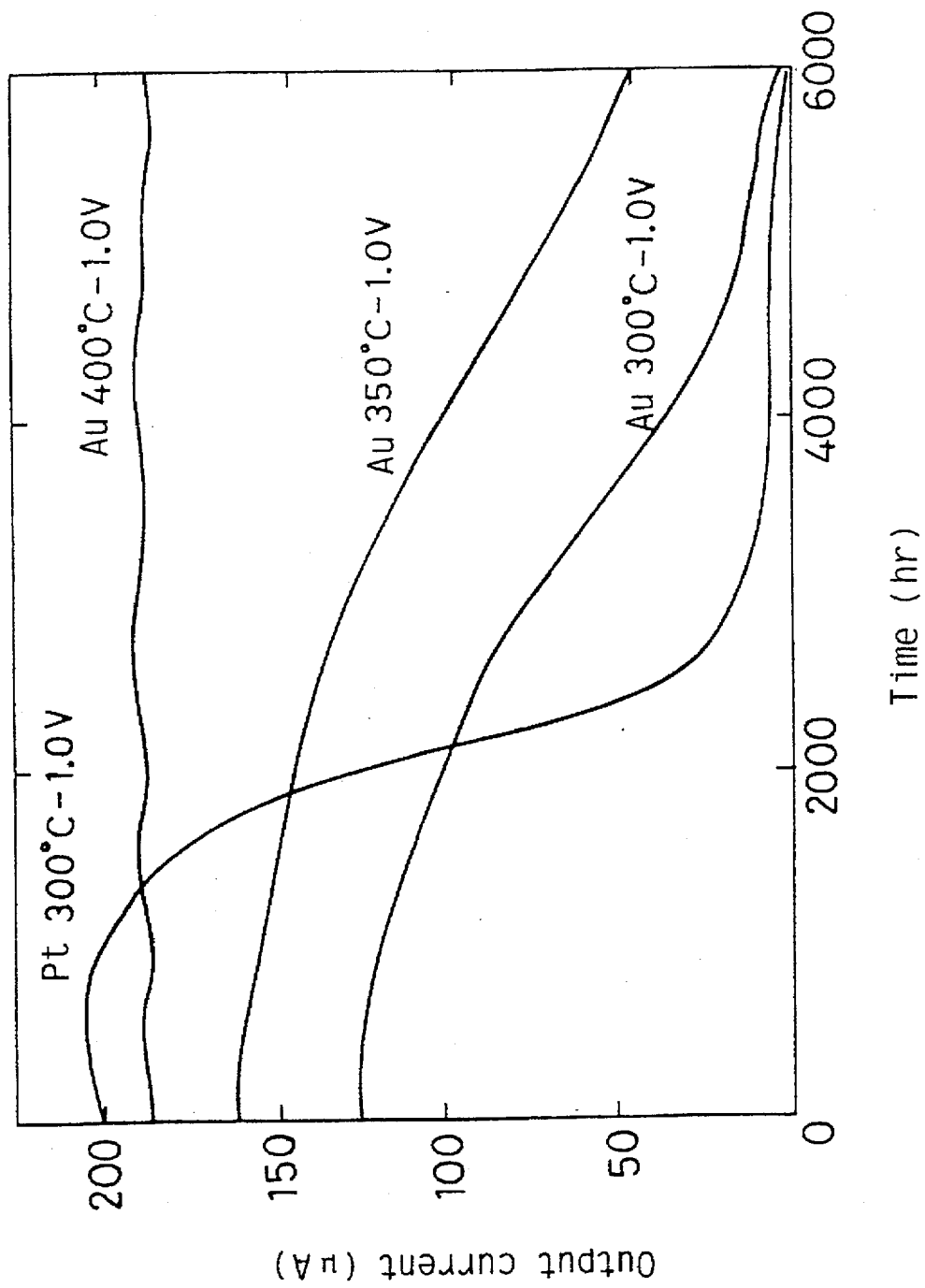
FIG. 8 is a graph showing limiting current features in the conventional limiting current type oxygen sensor.

When voltage-ampere characteristics were measured in this oxygen sensor, a higher current value was obtained as compared with the sensor using the pure gold electrode. Even at 300° C., a satisfactory limiting current characteristic was observed in this sensor. When a voltage of 1.0 V was applied between both electrodes, the limiting current observed was proportional to the oxygen concentration. Oxygen sensors having various platinum contents in both electrodes were placed in an air atmosphere at 300° C. while applying a voltage of 1.0 V between both electrodes. Then, current deterioration rate was measured after 5,000 hours to compare with the initial current value. The results are shown in FIG. 5. As indicated in FIG. 5, samples in which the mixing ratio of platinum was 1, 3 or 5% by atom kept extremely excellent stability for long time.

Therefore, a gold electrode having a high thermal expansion coefficient can not be used as an electrode for low temperature operation without any treatment since the gold electrode itself is not active at low temperatures though it is physically very compatible with the barium-cerium complex oxide. However, if a small amount of platinum is mixed with gold, a catalytic effect occurs, and an electrode is obtained which is active even at low temperatures and has a very stable output. Namely, by using such materials for the electrode, there can be obtained a limiting current type oxygen sensor with less change in output current, having a longer life, allowing a stable operation at lower temperatures, as compared with the conventional example.

EXAMPLE 5

In this example, as the solid electrolyte, barium-cerium-yttrium oxide $BaCe_{0.8}Y_{0.2}O_{3-a}$ was used. The configuration of the solid electrolyte and production method of the oxygen sensor were the same as those in Example 4, except that a mixture obtained by mixing 1 to 11% by atom of platinum with silver was used for a cathode and an anode, respectively. These electrodes were made by forming a thick film (4 to 5 μm) by screen printing method, and firing the thick film at 900° C. for one hour.

Also in this example, the oxygen sensor showed the limiting current characteristic at 300° C. and the limiting current value was proportional to the oxygen concentration. When life tests were conducted with a continuous application of a voltage of 1.2 V at 300° C. as in Example 4, samples in which the mixing ratio of platinum was 1, 3 or 5% by atom showed a stable continuous output characteristic for long time as shown in FIG. 5.

In this way, even in the silver electrode, activation of the silver electrode at low temperatures is realized by mixing a small amount of platinum, and it is possible to produce a limiting current type oxygen sensor having a long service life with less adverse change in output current, allowing a stable operation at low temperatures, compared to the conventional oxygen sensor.

EXAMPLE 6

In the present example, as the solid electrolyte, the same barium-cerium-gadolinium oxide $BaCe_{0.84}Gd_{0.16}O_{3-a}$ as applied in Example 3 was used. In this example, a mixture obtained by mixing 1 to 11% by atom of platinum with copper was used for a cathode and an anode, respectively.

Also in this example, the oxygen sensor showed the limiting current characteristic at 300° C. and the limiting current value was proportional to the oxygen concentration. When life tests were conducted with a continuous application of a voltage of 1.2 V at 300° C., samples in which the mixing ratio of platinum was 1, 3 or 5% by atom showed a stable continuous output characteristic for long time as shown in FIG. 5.

In this way, even in the copper electrode, activation of the copper electrode at low temperatures is realized by mixing a small amount of platinum, and it is possible to produce a limiting current type oxygen sensor having a long service life with less adverse change in output current, allowing a stable operation at low temperatures, compared to the conventional oxygen sensor.

In addition to the effects observed in Examples 4 and 5, this example has an additional effect such that less expensive material can be used to reduce the cost.

EXAMPLE 7

In the present example, a solid electrolyte thick film was formed by plasma spraying method. As a raw material, the same barium-cerium-gadolinium oxide $BaCe_{0.8}Gd_{0.2}O_{3-a}$ as applied in Examples 1 and 4 was used. First, a cathode obtained by mixing platinum with carbon was formed on one surface of a porous electrically insulating substrate by printing method. Then, a thick film of the barium-cerium-gadolinium oxide was formed on the substrate by the plasma spraying method. Further, on the thick film, an anode prepared from a mixture of platinum and carbon was formed on the thick film by printing. The thickness of the barium-cerium-gadolinium oxide was 45 μm. This largely reduced inner resistance of the solid electrolyte compared with those of the examples as shown above. Further, the operating temperature could be lowered to 100° to 200° C. In this way, use of a carbon electrode enables operation of an electrochemical device at low temperatures and reduction of cost. In this example, a mixture obtained by mixing 1 to 11% by atom of platinum with carbon was used, too.

Also in this example, the oxygen sensor showed the limiting current characteristic at 150° C. and the limiting current value was proportional to the oxygen concentration. When life tests were conducted with a continuous application of a voltage of 1.2 V at 150° C., samples in which the mixing ratio of platinum was 1, 3 or 5% by atom showed a stable continuous output characteristic for long time compared to the conventional oxygen sensor, as shown in FIG. 5.

In this way, even in the carbon electrode used for the oxygen sensor in which the solid electrolyte thick film was used and which was designed to be used at lower temperatures, activation of the carbon electrode at low temperatures is realized by mixing a small amount of platinum, and it is possible to produce a limiting current type oxygen sensor having a long service life with less adverse change in output current, allowing a stable operation at low temperatures, compared to the conventional oxygen sensor.

Though the barium-cerium-gadolinium oxides $BaCe_{0.8}Gd_{0.2}O_{3-a}$ and $BaCe_{0.84}Gd_{0.16}O_{3-a}$ were used respectively as a solid electrolyte in Examples 1, 3, 4, 6 and 7, other solid electrolytes having different cerium and gadolinium contents can be used. Further, though $BaCe_{0.8}Y_{0.2}O_{3-a}$ was used in Examples 2 and 5, a barium-cerium complex oxide which has been added with a rare earth element other than Gd or Y can be used.

Further, though platinum was used as an electrode material in Examples 1, 2 and 3, materials such as Ag, Pd and the like can be used.

Also, though platinum was used as a thin film electrode material in Examples 1, 2 and 3, materials such as Au, Ag, Pd and the like can be used.

And, though in Examples 1, 2 and 3, sputtering method was used for producing a thin film electrode, any other method may be used provided that it enables production of a thin film (not more than 1 μm) from a pure material, such as vacuum deposition, CVD, printing and firing of a metallo-organic paste or the like.

In Examples 4 to 7, though metal or carbon mixed with platinum was used for both cathode and anode, platinum may be added to either one of the cathode and the anode.

For producing the electrode, though printing method was used in Examples 4 to 7, a thin film electrode can be produced by using a production method such as sputtering, vacuum deposition, CVD or the like.

In the above-described examples, although a limiting current type oxygen sensor was used as an electrochemical device to reveal the effectiveness of a barium-cerium complex oxide in an electrode site, the present invention exerts the same effectiveness when applied to other electrochemical devices such as a fuel cell, oxygen pump and the like.

As described above, according to the present invention, there can be obtained a long lasting and highly reliable electrochemical device as compared with an electrochemical device using the conventional barium-cerium complex oxide.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. An electrochemical device comprising a layer of a barium-cerium complex oxide, a cathode formed on one surface of the layer of said barium-cerium complex oxide and an anode formed on another surface of the layer of said barium-cerium complex oxide, wherein at least one of said anode and cathode is so-configured as a thin film electrode free from organic binder and glass frit to alleviate the difference in thermal expansion coefficient from said barium-cerium complex oxide.

2. The electrochemical device in accordance with claim 1, wherein at least one of the anode and the cathode is formed to have a layered structure comprising a first thin film electrode formed on said surface of the layer of the barium-cerium complex oxide and a second electrode formed on said first thin film electrode.

3. The electrochemical device in accordance with claim 1, wherein at least one of the anode and cathode comprises a mixture of platinum and one element selected from the group consisting of gold, silver, copper and carbon.

4. The electrochemical device in accordance with claim 3, wherein a mixing ratio of platinum is not more than 5% by atom.

5. The electrochemical device in accordance with claim 1, wherein said barium-cerium complex oxide is an oxide represented by the formula $BaCe_{1-x}M_xO_{3-a}$, wherein M is at least one element selected from the group consisting of Sc, Y, La, Pr, Nd, Pm, Sm, Eu, Gd, Tb, Dy, Ho and Er, and wherein $0<x<1$ and $0<a<1$.

6. The electrochemical device in accordance with claim 5, wherein $0.16 \leq x \leq 0.23$.

7. The electrochemical device in accordance with claim 5, wherein M is Gd, and wherein $0.16 \leq x \leq 0.23$.

8. The electrochemical device in accordance with claim 7, wherein said barium-cerium complex oxide is an oxide represented by the formula $BaCe_{0.8}Gd_{0.2}O_{3-a}$, wherein $0<a<1$.

9. The electrochemical device in accordance with claim 1, wherein the first thin film electrode of the anode or the cathode comprises Pt, Pd, Au or Ag.

10. The electrochemical device in accordance with claim 1, further comprising a mechanism that restricts oxygen diffusion on the cathode side.

* * * * *